United States Patent

Kohayakawa

[11] Patent Number: 5,995,759
[45] Date of Patent: Nov. 30, 1999

[54] STEREOSCOPIC IMAGE APPARATUS

[75] Inventor: Yoshimi Kohayakawa, Utsunomiya, Japan

[73] Assignee: Canon Kabushiki Kaisha, Japan

[21] Appl. No.: 08/985,738

[22] Filed: Dec. 5, 1997

[30] Foreign Application Priority Data

Dec. 10, 1996 [JP] Japan .................................. 8-346769

[51] Int. Cl.⁶ .................................................. G03B 29/00
[52] U.S. Cl. ............................ 396/18; 396/323; 396/324; 348/78
[58] Field of Search .................................... 396/323, 330, 396/18; 348/45, 46, 51, 54, 55, 56, 59, 67, 78

[56] References Cited

U.S. PATENT DOCUMENTS

| | | | |
|---|---|---|---|
| 3,731,606 | 5/1973 | Geoffray | 396/330 |
| 4,248,505 | 2/1981 | Muchel et al. | 351/7 |
| 4,488,795 | 12/1984 | Winnek | 396/330 |
| 4,668,063 | 5/1987 | Street | 396/330 |
| 4,717,952 | 1/1988 | Kohayakawa | 358/113 |
| 4,867,554 | 9/1989 | Matsumura | 351/205 |
| 5,018,851 | 5/1991 | Matsumura | 351/214 |
| 5,713,047 | 1/1998 | Kohayakawa | 396/18 |

FOREIGN PATENT DOCUMENTS 8-182650  7/1996  Japan ............................. A61B 3/028

*Primary Examiner*—David M. Gray
*Attorney, Agent, or Firm*—Fitzpatrick, Cella, Harper & Scinto

[57] ABSTRACT

An eye imagining apparatus where, in the case of a stereoscopic image, a beam from a left stop of a stereoscope stop and a beam from a right stop of the stereoscopic stop form an eye fundus image on a surface of a cylindrical lens array. These beams also reach adjacent image pickup device elements of an image pickup device of an image pickup unit, respectively. With the cylindrical lens array having the pitch width corresponding to two image pickup device elements, the focal length is determined so that an image of the stereoscope stop is focused in the pitch width, and the imaging plane of the cylindrical lens array is focused on the image pickup device by relay lens apparatus. On the other hand, with a monocular image, a single stop plate is put in the optical path instead of the stereoscope stop and the cylindrical lens array is retracted from the optical path, whereby the image is photographed with a higher horizontal image definition.

7 Claims, 8 Drawing Sheets

STEREOSCOPIC IMAGE APPARATUS

BACKGROUND OF THE INVENTION

1. Field of the Invention

The present invention relates to a stereoscopic image apparatus applicable to an eye fundus camera and the like.

2. Related Background Art

Dedicated devices for separately recording right and left images are conventionally known as stereoscopic image apparatus and particularly, simultaneous, stereoscopic eye fundus photographing cameras are dedicated devices for stereoscopic photography with two photographing optical systems for right and left images. For photography of stereoscopic image, two images are separately photographed on separate medium surfaces from right and left. Especially, when an image on an operation microscope is stereoscopically photographed, images of respective optical paths of right and left eyes are recorded by using two TV cameras, they are displayed on one TV monitor in time division, and they are observed through time-division stereoscopic spectacles.

However, since the stereoscopic image devices of the above-stated conventional examples are dedicated devices for stereoscopic photography, their structure is complex. In the case of an endoscope, two CCDs are used for image pickup. In the case of a stereophotographic, eye fundus camera, images are taken in a film having two frames. The photographing apparatus is big and complex in either case. A device for displaying a stereoscopic image by use of a cylindrical lens array has a problem in that the image will not appear stereoscopic unless the position of observer's face is appropriate, and it is thus hard to find where the display screen should be watched for stereoscopic view.

Since the images for the right and left eyes are projected to a transmission type screen with the cylindrical lens array, the structure of the projecting device is complex and positioning of right and left images is difficult. A further problem is a complex photographing operation, because the respective images for the right and left eyes are separately photographed.

SUMMARY OF THE INVENTION

A first object of the present invention is to provide a stereoscopic image apparatus capable of being used for both stereoscopic imaging such as photography and monocular imaging such as photography.

A second object of the present invention is to provide a stereoscopic image apparatus in which an appropriate position of a face can readily be found upon observation.

A third object of the present invention is to provide a stereoscopic image apparatus for displaying an enlarged view of a stereoscopic image in which right and left eye images are composed alternately of vertical lines of pixel pitch.

A fourth object of the present invention is to provide a stereoscopic image apparatus having a compact photographing device of simple structure.

The other objects of the present invention will become apparent in the description of embodiments which follows.

DESCRIPTION OF THE PREFERRED EMBODIMENTS

The present invention will be described in detail, based on the embodiments illustrated.

Figure 1:
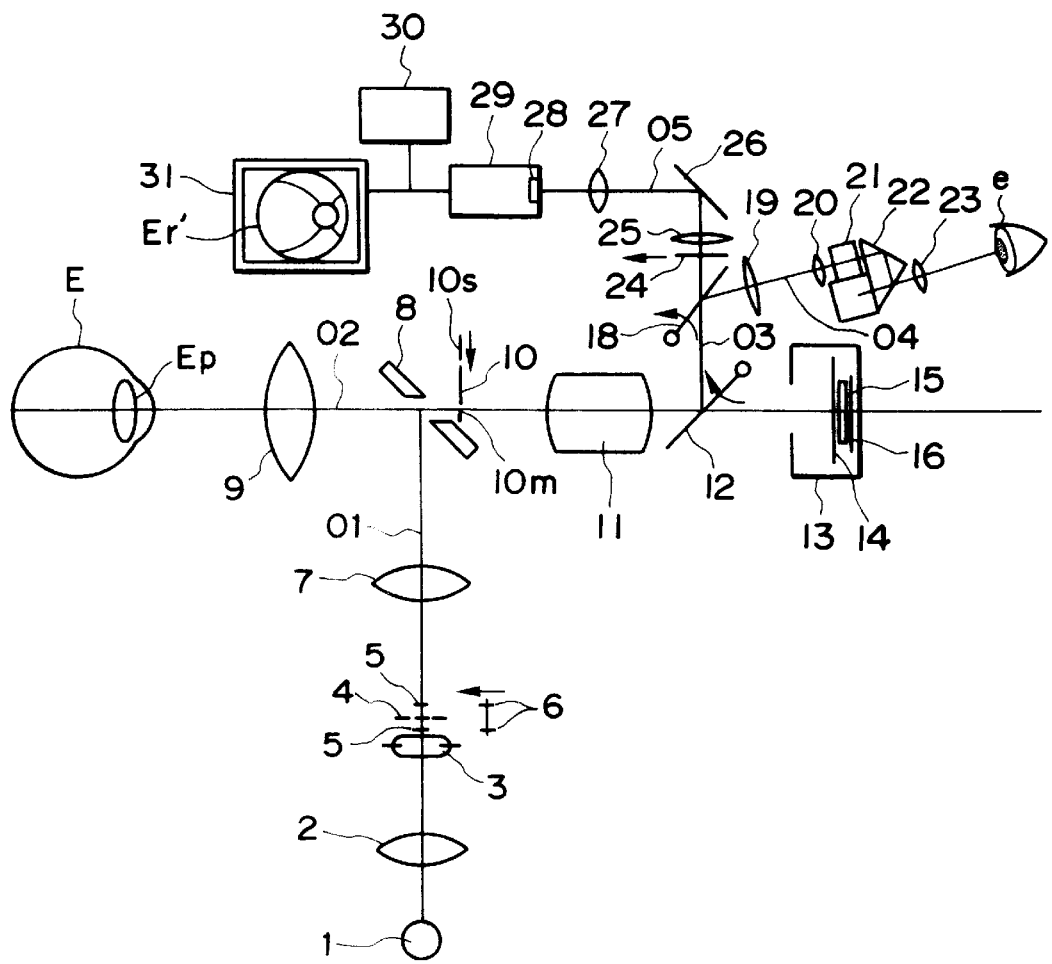
FIG. 1 is a structural drawing of the first embodiment.
Figure 2:
FIG. 2 is a front elevation of a shield member.

FIG. 1 is a structural drawing of an eye fundus photographing apparatus capable of undergoing stereoscopic photography and monocular photography, in which there are the following elements arranged in order on optical path 01 of an illumination optical system: light source 1 for illumination of eye fundus comprised of a halogen lamp, lens 2, flash light source 3 for photography, ring slit 4 conjugate with the anterior part of the eye, shield member 5 or 6 disposed before and after the ring slit 4 on the optic axis, lens 7, and bored mirror 8 having a horizontally elongated hole. The shield member 6 has a horizontally elongated shape as shown in FIG. 2, so that more beams are incident from above and below the pupil Ep into the eye. The shield member 6 is set on the optical path 01 as replacing the shield member 5 upon color magnification photography, stereoscopic photography, or fluorescent photography.

On optical path 02 of a photographing optical system there are the following elements arranged in order from the side of the observed eye E: objective lens 9, bored mirror 8, stop plate 10 having stereoscope stop 10s comprised of two, right and left stops for stereoscopic photography and single stop 10m for monocular photography, the stereoscope stop 10s and single stop 10m being arranged to be selected in alternative fashion, imaging lens 11 including a focus lens and a variable-power lens, changeover mirror 12, and film camera 13. The film camera 13 incorporates shutter 14, cylindrical lens array 15, and film 16.

When the film 16 is 35-mm film, the cylindrical lens array 15 is an array of cylindrical lenses arranged at the pitch of about 20 μm and having the generatrices along the vertical direction. The cylindrical lens array 15 makes the surface of film 16 conjugate with the stop plate 10 and an eye fundus image is focused on the cylindrical lens array 15. Right and left images are formed alternately in vertical stripe patterns on the film 16. Further, upon monocular photography, an eye fundus image is formed in fine stripe patterns of about 30 μm as not to obstruct the view.

Changeover mirror 18 is located on optical path 03 in the direction of reflection of the changeover mirror 12. The changeover mirror 18 changes the optical path 03 over to optical path 04 of a finder optical system. On the optical path 04 there are the following elements arranged in order: field lens 19, relay lens 20, split prism nearly conjugate with the pupil Ep, porro prism 22 comprised of two rectangular prisms, and eyepiece 23, and the optical path finally reaches the examiner's eyes e.

Figure 3:
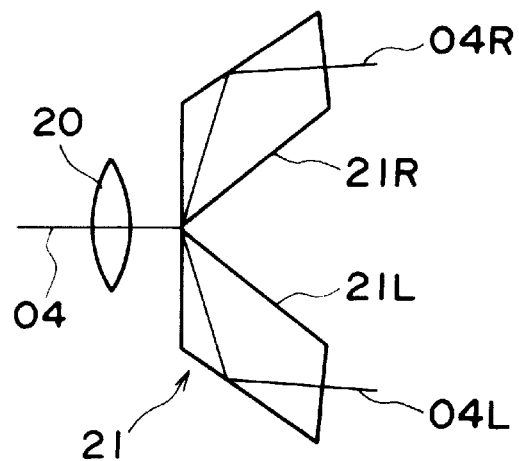
FIG. 3 is a plan view of a split prism.

The split prism 21 is composed of two prisms 21R, 21L having their normal lines on the same plane and each having four non-parallel surfaces, as shown in FIG. 3. The two prisms 21R, 21L split the optical path 04 into two optical paths 04R, 04L. Further, for easy observation with some convergence to the examiner's eyes e, the optical paths 04R and 04L have the divergence at 7 to 8 degrees. This causes the right and left eyes to observe the pupil Ep from right and left even in use of the monocular stop plate 10m, as well as in use of the stereoscopic stop 10s, thus permitting the examiner's eyes e to experience more or less stereoscopic observation in either case.

On the other hand, on the optical path 05 of the photographing optical system extending along an extension of the optical path 03, there are the following elements arranged in order: cylindrical lens array 24 capable of being mounted or dismounted on the optical path 05 near the imaging plane, field lens 25, mirror 26, relay lens 27, and image pickup means 29 provided with image pickup device 29 having two image pickup device elements 28L, 28R of area array sensors. The output of image pickup means 29 is connected to video recorder 30 and to TV monitor 31 provided with a cylindrical lens array.

Based on the structure described above, light from the light source 1 for illumination of eye fundus is condensed on the ring slit 4 by the lens 2, the light is again condensed via the shield member 5 on the bored mirror 8 by the lens 7, the light is reflected by the mirror portion at the periphery of the bored mirror 8, and then the light is projected onto the eye fundus of examinee's eye E through the objective lens 9. Reflected light from the eye fundus passes the objective lens 9, the hole part of the bored mirror 8, stop plate 10, imaging lens 11, changeover mirrors 12, 18, field lens 19, relay lens 20, split prism 21, porro prism 22, and eyepiece 23 to enter the examiner's eyes e, whereby the eye fundus image R is observed by the examiner.

When the changeover mirror 18 is flipped up from the optical path 03, the light advances on the optical path 05 to pass the cylindrical lens array 24, field lens 25, mirror 26, and relay lens 27 and then the images are picked up by the image pickup device 28 of the image pickup means 29. Then the eye fundus image R is displayed on the TV monitor 31 and recorded in the video recorder 30.

Upon photography on the film, the flash light source 3 emits light and the light passes through the same optical path as upon observation, thereby illuminating the eye fundus. Reflected light from the eye fundus passes through the optical path 02 and the changeover mirror 12 is flipped up. Thus, the eye fundus image R is photographed on the film 16 through the shutter 14 and cylindrical lens array 15.

Figure 4:
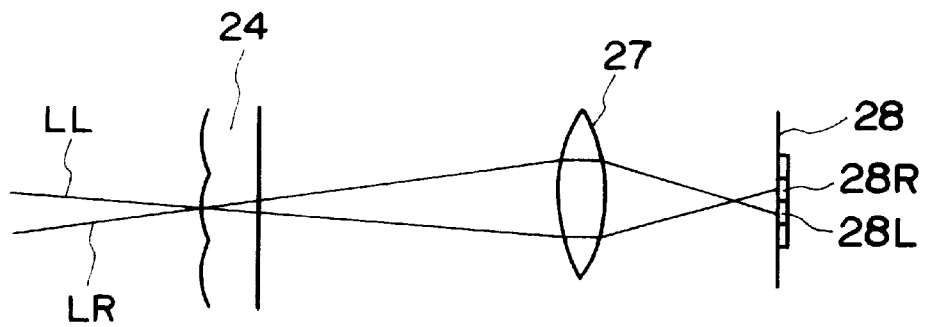
FIG. 4 is a structural drawing of a photographing optical system.

FIG. 4 is a structural drawing of the image pickup optical system, in which the cylindrical lens array 24 and image pickup device 28 are depicted as enlarged. Beam LL through the left stop of the stereoscope stop 10s and beam LR from the right stop thereof form eye fundus image Er' on the surface of cylindrical lens array 24 and then reach the adjacent image pickup device elements 28L, 28R, respectively, of the image pickup device 28 of the image pickup means 29. The focal lengths are so set that the cylindrical lens array 24 having the pitch width corresponding to two image pickup device elements 28L, 28R can form the image of stereoscopic stop 10s in the pitch width. The imaging plane of the cylindrical lens array 24 is focused through the relay lens 27 on the image pickup device 28. The mounting and dismounting arrangement of the cylindrical lens array 24 is employed herein, because the image pickup device normally has an insufficient number of pixels, different from the film 16, and horizontal definition of image thus needs to be increased upon monocular photography. Accordingly, mounting/dismounting is unnecessary, if the number of horizontal device elements is enough.

Figure 5:
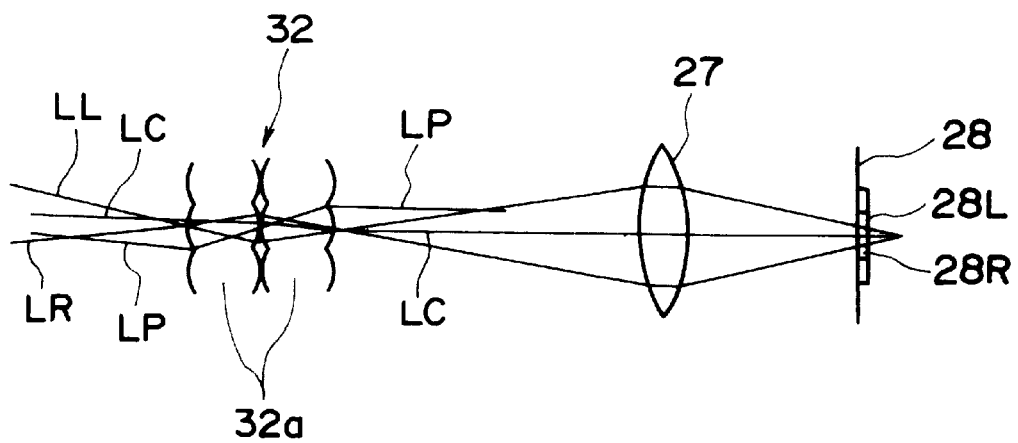
FIG. 5 is a structural drawing of the second embodiment.

FIG. 5 is a structural drawing of the second embodiment of the photographing optical system, which employs cylindrical lens array 32 in place of the cylindrical lens array 24 on the optical path 05. This cylindrical lens array 32 is a stack of two identical cylindrical lens arrays 32a. The image pickup device 28 is positioned in such positional relation that the two beams LL, LR passing the center of stereoscope stop 10s reach the centers of adjacent image pickup device elements 28L, 28R.

Owing to this arrangement, beam LP impinging on the periphery of an element of the array 32 also passes the optical path shown in FIG. 5 so as not to diverge after passage through the cylindrical lens array 32, similar to beam LC impinging on the center of the element of the cylindrical lens array 32. Therefore, the aperture of relay lens 27 can be decreased. The eye fundus image Er' formed by the imaging lens 11 is focused on the front surface of cylindrical lens array 32 and thereafter it is further refocused on the back surface thereof by the cylindrical lens action.

Figure 6:
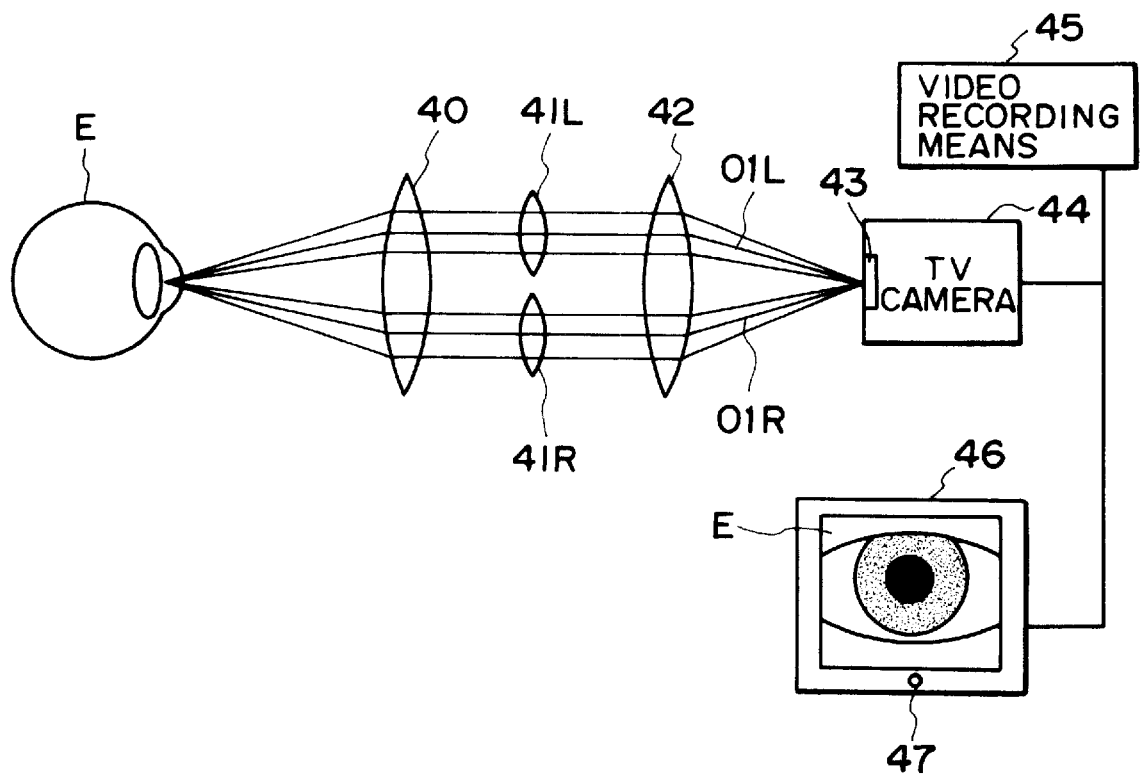
FIG. 6 is a structural drawing of the third embodiment.

FIG. 6 is a plan view of an application in which the present invention is applied to a microscope for operation, as the third embodiment, wherein there are the following elements arranged in order from the examinee's eye E: objective lens 40 common to the right and left eyes, optical systems 41L, 41R separately provided for the left and right eyes, each including an afocal variable-power optical system, imaging lens 42, and TV camera 44 having image pickup device 43 of area CCD or the like. The output of TV camera 44 is connected to video recording means 45 and to TV monitor 46, and the TV monitor 46 is provided with positioning means 47 for positioning the observer's face.

Figure 7:
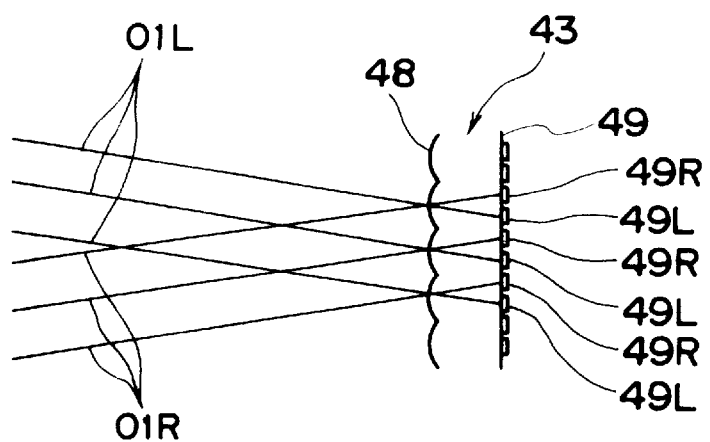
FIG. 7 is an explanatory drawing of beams near an image pickup surface.

The image pickup device 43 is provided with cylindrical lens array 48 as shown in FIG. 7. The left and right beams O1L, O1R are received by separate sensor elements 49L, 49R, respectively, and images observed from left and right are picked up by even pixels and odd pixels, respectively, in the horizontal direction. Since the generating lines of cylindrical lens array 48 extend vertically, i.e., normally to the plane of the drawing, the array pitch thereof is coincident with the pitch of each of the sensor elements 49L, 49R, and the focal length of cylindrical lens array 48 is determined so that the exit pupil of the imaging optical system is focused in the approximate same size as the light-receiving aperture of sensor elements 49L, 49R in the plane of the drawing. The cylindrical lens array 48 may be replaced by a slit array having slit apertures arranged at the same pitch.

The left and right beams O1L, O1R from the examined eye E pass through the common objective lens 40 to become parallel beams and then pass the left and right optical systems 41L, 41R. Then they are focused on the image pickup device 43 of TV camera 44 by the imaging lens 42, and images of the examined eye E are formed near the surface of cylindrical lens array 48. A signal of TV camera 44 is displayed on the TV monitor 46 and recorded in the video recording means 45. The TV monitor 46 is provided with a cylindrical lens array having the pitch of pixel pair and the generatrix in the vertical direction. The left and right images are projected onto the left and right eyes of the observer (not illustrated). This observing device is described in the visual function examining apparatus of Japanese Laid-open Patent Application No. 8-182650.

In an apparatus for observing a stereoscopic image by use of the cylindrical lens array 48, if the image is observed in such a manner that beams passing through adjacent elements of cylindrical lens array 48 are made incident respectively on the left and right eyes, the front and rear relation will appear reversed: and it will pose a problem of occurrence of reversed depths depending upon positions of observation. Therefore, beams through one element of cylindrical lens array 48 are made incident to the left and right eyes.

Figure 8:
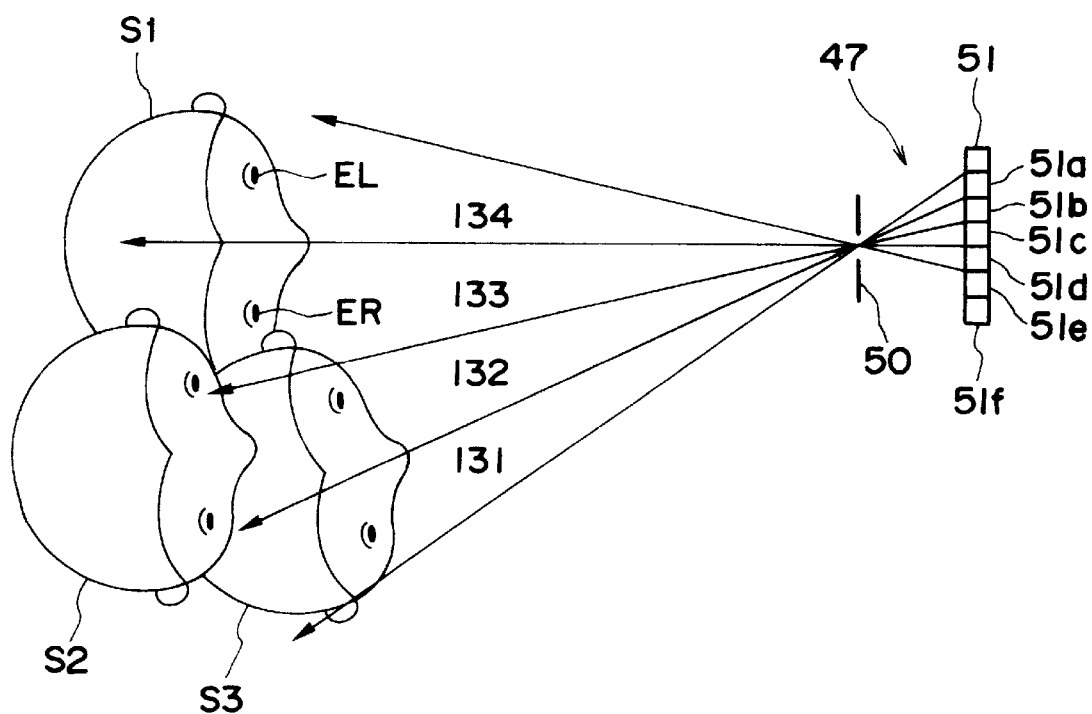
FIG. 8 is an explanatory drawing of positioning beams.

FIG. 8 is an explanatory drawing of positioning beams of positioning means 47, wherein the positioning means 47 of TV monitor 46 is composed of vertical slit aperture 50 and light source 51 consisting of plural elements. The slit aperture 50 is located on the surface of cylindrical lens and is constructed in such structure that the slit width corresponds to one cylindrical lens element so as to shield the cylindrical lens elements adjacent thereto. The light source 51 is arranged so that each of the light source elements 51a to 51f projects a beam having the same spread in the same direction as each of the display pixel does by an element of the cylindrical lens 48 of TV monitor 46 in the plane of the drawing.

Figure 9:
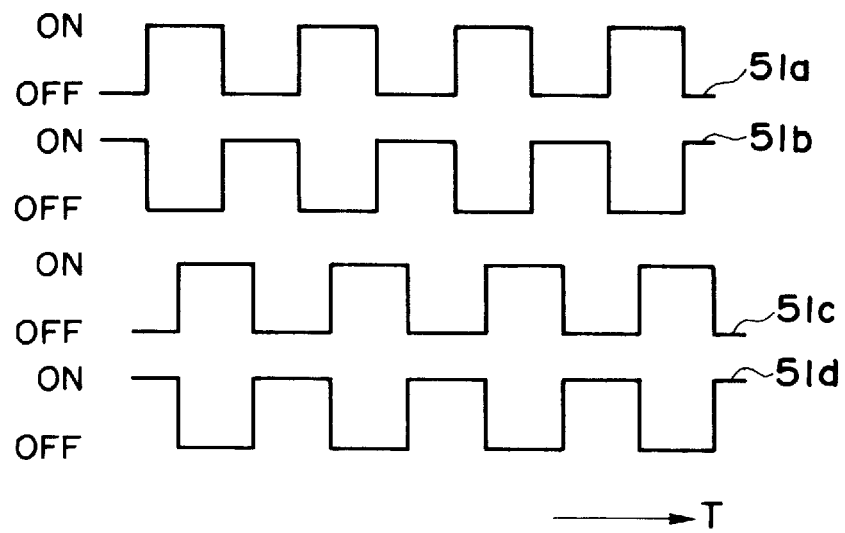
FIG. 9 is a timing chart of on timing of positioning beams.

FIG. 9 is a timing chart to show on timing of the light source elements 51a to 51d of light source 51, in which the abscissa represents time T. The light source elements 51a and 51b or the light source elements 51c and 51d each become on in 180°-shifted phases, i.e., in the opposite phases, and the light source elements 51c and 51d have a phase difference of 90° relative to the light source elements 51a and 51b. When the observer is at the position of S1, beams from the respective light source elements 51d, 51c are incident to the left and right eyes EL, ER, respectively. Thus, they are perceived as a continuously lit light. This position is a position where the observer can observe the TV monitor 49 through the same cylindrical lens element.

When the observer is at the position of S2, the beam from the light source element 51c enters the left eye EL and the beam from the light source element 51b enters the right eye ER. Thus, they are perceived as flickering light and this position corresponds to a position where one eye observes the surface of TV monitor 49 through an adjacent cylindrical lens element. Further, with the observer at the position of S3 the left and right eyes EL, ER observe the beams from the light source elements 51b, 51a, respectively, which become complimentarily on in the opposite phases. Thus, they are perceived as a continuously lit light. This position thus corresponds to a position where the both eyes observe the screen of TV monitor 46 through the adjacent cylindrical lens element. The light source elements 51e, 51f are turned on in the same phases as the light source elements 51a, 51b. In this way the observer observes the TV monitor 46 while the face is located at a non-flickering position of light source 51.

The positioning means 47 may use a part of the screen of TV monitor 46. In this case the light source elements of light source 51 are emission elements of TV monitor 46 and each of the emission elements emits a positioning beam at the same timing as in FIG. 9.

Figure 10:
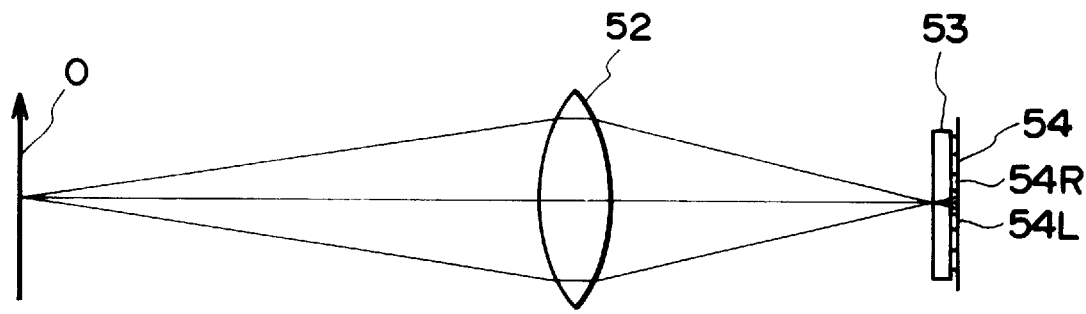
FIG. 10 is a structural drawing of the fourth embodiment.

FIG. 10 is a structural drawing of the fourth embodiment, wherein cylindrical lens array 53 and photographic film 54 are located on the imaging plane of single imaging lens 52. The cylindrical lens array 53 may be replaced by a slit array.

An image of object O is formed by the imaging lens 52 on the surface of cylindrical lens array 53 having the generating lines normal to the plane of the drawing, and the cylindrical lens array 53 focuses the exit pupil of imaging lens 52 on the film 54 located behind it. The pitch of the cylindrical lens array 53 is determined by necessary resolving power. For example, when the 35-mm film is used in the eye fundus camera, the pitch is determined to be about 20 $\mu$m. The focal length of cylindrical lens array 53 is determined so that the exit pupil of imaging lens 52 is focused in the pitch width. On the film 54 image 54L by the beam passing the right side of imaging lens 52 and image 54R by the beam passing the left side thereof are photographed in laterally alternate strip patterns.

Figure 11:
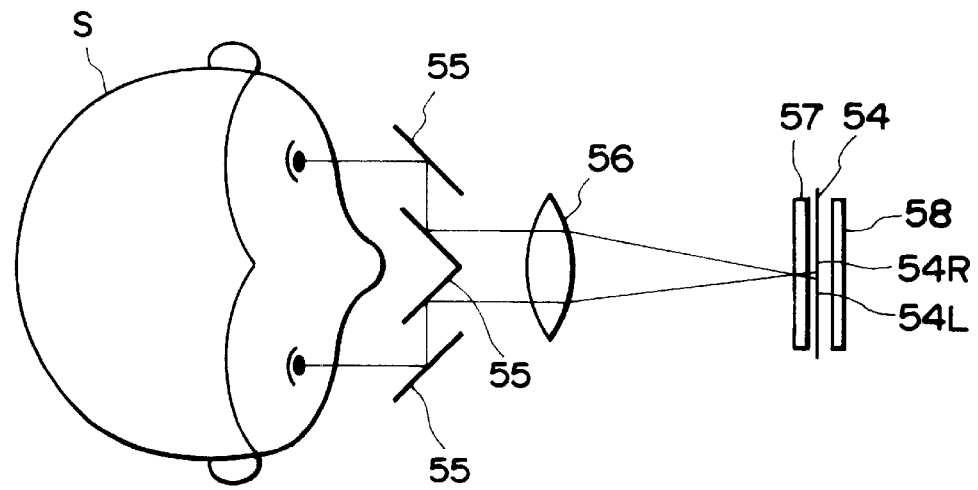
FIG. 11 is a plan view of observing means.

FIG. 11 is a plan view of observing means for observing the photographed film 54, in which magnifying lens 56, cylindrical lens array 57 located near the focal point of the magnifying lens 56, the film 54, and light source 58 are arranged in order on optical paths of reflected light from four mirrors 55 disposed in front of the observer S. The direction and pitch of the cylindrical lens array 57 are the same as those of the cylindrical lens array 53, and the focal length thereof is determined so that the width of one-side pixel 54R or 54L is magnified to approximately 20 mm before the eyes of the observer S. When the observing means is of a type capable of adjusting the eye width by moving the outside mirrors 55 in the direction of eye width, the width may be approximately 10 mm.

The light source 58 illuminates the photographed film 54 from the back, and the images 54L, 54R of the object O on the film 54 are projected via the cylindrical lens array 57, magnifying lens 56, and four mirrors 55 respectively onto the both eyes of the observer S. The observer S observes the image 54L by the left eye and the image 54R by the right eye, thus stereoscopically viewing the object O. When the film 54 and cylindrical lens array 57 are separated from each other as in this case, mutual positioning becomes necessary. Therefore, the arrangement may be so modified that they are preliminarily positioned to each other and incorporated and that they are put together into the observing means. Further, it can also be contemplated that the object is photographed on a film having the cylindrical lens array and the film is also observed through the cylindrical lens array of the same direction and pitch upon observation.

Figure 12:
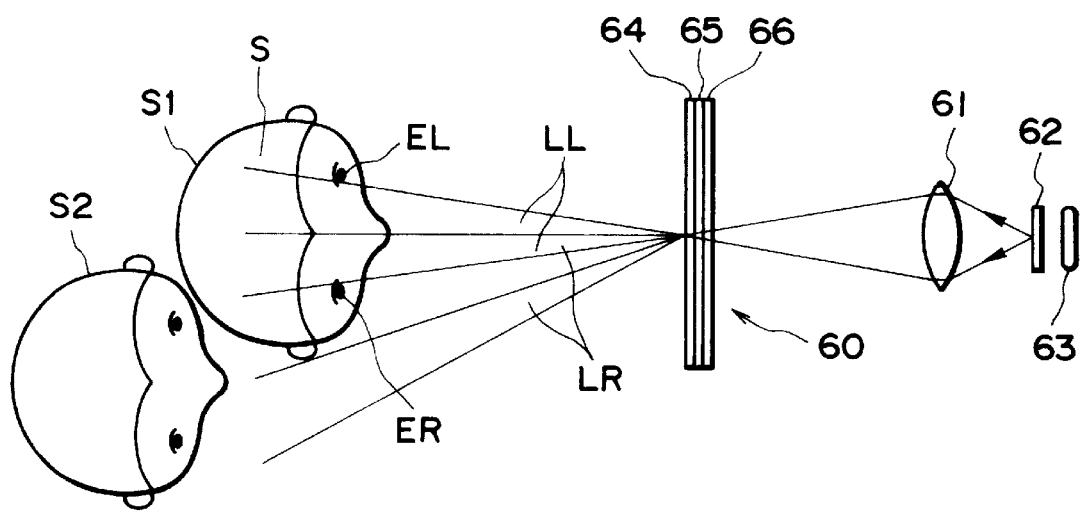
FIG. 12 is a structural drawing of the fifth embodiment.
Figure 13:
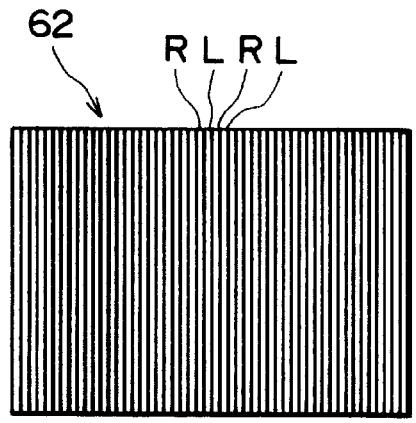
FIG. 13 is a front elevation of an image display member.

FIG. 12 is a plan view of a stereoscopic image magnifying projection apparatus of the fifth embodiment, in which from the side of observer S there are the following elements arranged in order: transmission type screen 60, taking lens 61, image display member 62 such as a transmission type liquid-crystal display for TV or a photographic slide, and light source 63. Images L, R for the left and right eyes are displayed or recorded alternately in vertical stripe patterns of the pixel pitch in the image display member 62, as shown in FIG. 13. The screen 60 is composed of cylindrical lens array 64 having the generating lines extending along the vertical direction, diffuse plate 65, and Fresnel lens 66. The screen 60, taking lens 61, image display member 62, and light source 63 are incorporated integrally.

The image display member 62 is illuminated by the light source 63 located behind it, and an image thereof is projected as magnified onto the transmission type screen 60 by the projection lens 61.

Figure 14:
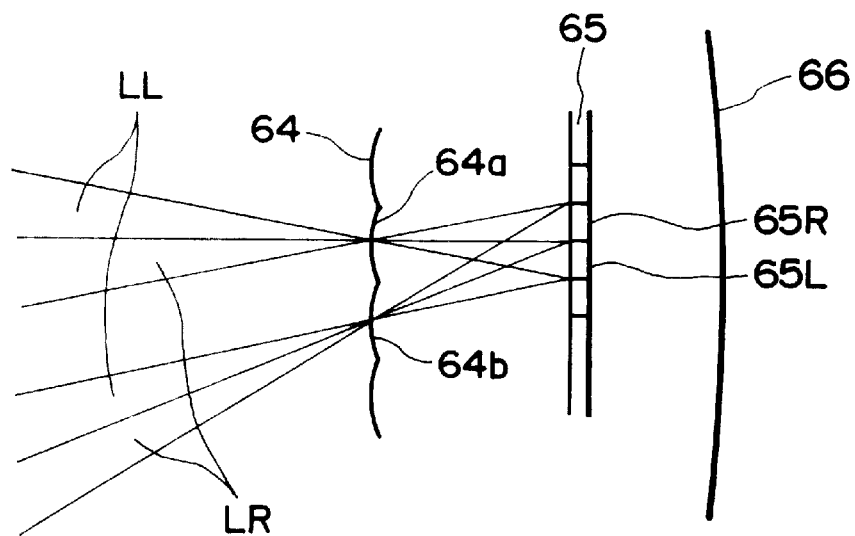
FIG. 14 is an explanatory drawing of beams in a screen portion.

FIG. 14 is a partly enlarged view of the screen 60, in which left and right image elements L, R of the image display member 62 are projected as magnified to elements 65L, 65R on the diffuse plate 65. Each of elements 64a, 64b of the cylindrical lens array 64 is almost the same in width with the left and right eye image elements 65L, 65R, but precisely, the element 64a, 64b is smaller than the elements 65L, 65R by a ratio of a distance from the diffuse plate 65 to the observer S and a distance from the cylindrical lens array 64 to the observer S. Therefore, a beam from the center of screen 60 and a beam from the periphery of screen 60 come to meet each other at the position of observer S.

Beams LL, LR from the elements 65L, 65R are incident on the left and right eyes, respectively, at the positions of S1, S2 of the observer S. When the observer S is located at the position of S1 just in front of the screen 60, the observer observes an image by the beams passing through the cylindrical lens element 64a located just in front of the pixel elements 65L, 65R. At the position of S2 a little shifted horizontally, the observer observes an image through the adjacent cylindrical lens element 64b. The number of cylindrical lens elements 64a, 64b is approximately 500 in the case of TV or approximately 2000 in the case of film projection. If observation is limited to only one observer S the diffuse member 65 will be unnecessary. Thus, the structure of apparatus can be made simpler and the cylindrical lens array 64 can be disposed near the image display member 62.

Figure 15:
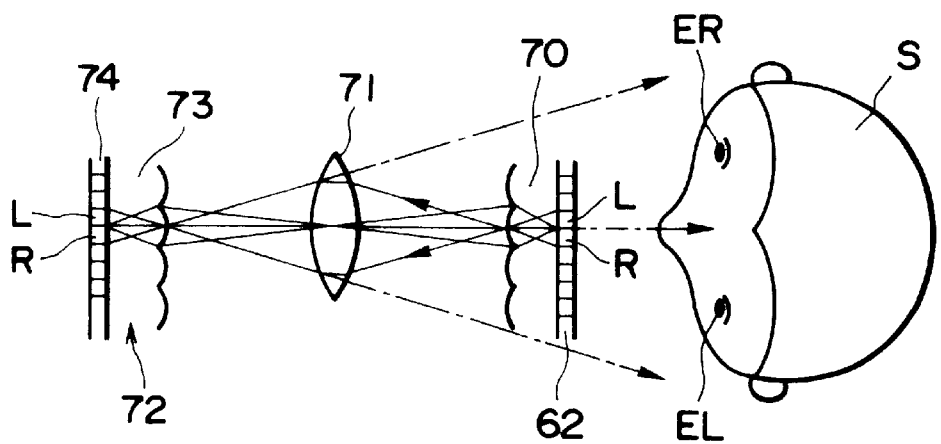
FIG. 15 is a structural drawing of the sixth embodiment.

FIG. 15 is a plan view of an application wherein the present invention is applied to a stereoscopic image projection apparatus using a reflection type screen as the sixth embodiment, in which the display member 62 and cylindrical lens 70 are drawn as enlarged. Arranged in order from the side of observer S are image display member 62 similar to that in the fifth embodiment, cylindrical lens array 70 of the pitch equal to the width of left and right eye elements L+R, located near the image display member 62, and projection lens 71, thereby composing a projector. Reflective screen 72 is positioned by several meters apart from the projection lens 71. The reflective screen 72 is composed of cylindrical lens array 73 having the pitch of the left and right eye pixels and the direction of the generating lines extending vertically, and diffuse reflection member 74. Illustration of the light source for illuminating the image display member 62 from the back is omitted.

The left and right eye elements L+R are projected onto the pupil of projection lens 71 by the cylindrical lens element and the projector magnifies and projects an image onto the reflective screen 72. The element of cylindrical lens array 73 projects the pupil of lens 71 onto the surface of diffuse reflection member 74, and the observer S observes the image reflected by the surface of diffuse reflection member 74 through the cylindrical lens array 73 but not through the projection lens 71 as shown by the dotted lines. Since the screen 72 diffusely reflects the light, the image can be observed by a plurality of observers S in the same manner as in the fourth embodiment. However, if the number of observer S is limited to one, the structure of apparatus can be made simpler. Specifically, the screen 72 may be a concave mirror having the simple field lens action. In this case, the concave mirror projects the pupil of projection lens 71 onto the observer S.

Figure 16:
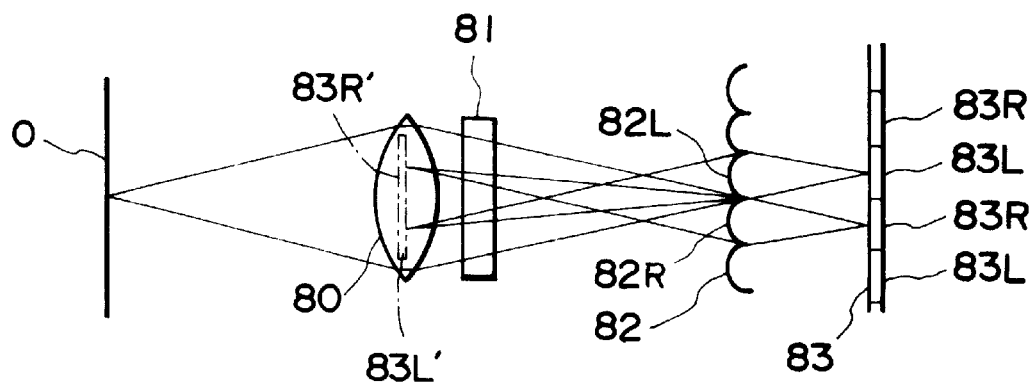
FIG. 16 is a structural drawing of the seventh embodiment.
Figure 17:
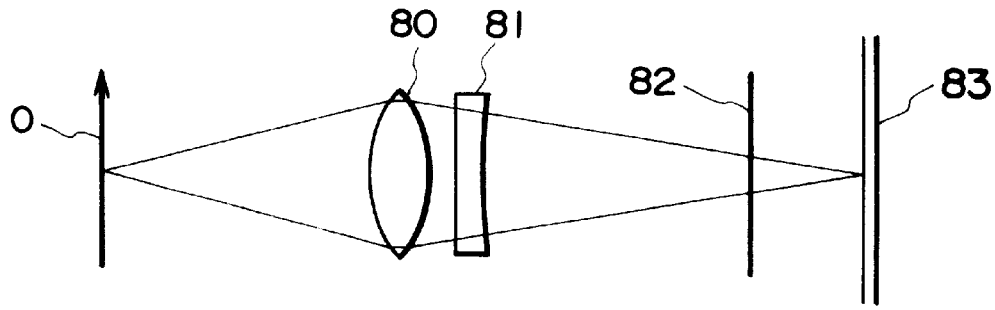
FIG. 17 is a side view.

FIG. 16 is a plan view of an application wherein the present invention is applied to a stereoscopic image photographing apparatus of the seventh embodiment and FIG. 17 is a side view thereof in which the cylindrical lens array portion is depicted as enlarged. Arranged in order from the side of object O are lens 80, cylindrical lens 81, cylindrical lens array 82, and photographic medium 83 such as a CCD image pickup device or a photographic film. The cylindrical lens array 82 is composed of element pairs 82L, 82R corresponding to pixel pairs 83L, 83R of photographic medium 83, and the pitch thereof is approximately 10 μm, equal to the pitch of pixels of photographic medium 83. The elements 82L, 82R of cylindrical lens array 82 have the prism action with decentering in the direction to approach each other, and the focal length thereof is 0.2 mm to 0.3 mm. When the depth of focus is deep as in the eye fundus camera, the cylindrical lens 81 can be omitted.

The light from the object O passes through the lens 80 and cylindrical lens 81 to focus the image of object on the surface of cylindrical lens array 82 in the plan view as shown in FIG. 16 and to focus the image on the surface of photographic medium 83 in the side view as shown in FIG. 17. According to the prism action of cylindrical lens array 82, the pixel 83L of photographic medium 83 is projected as 83L' on the left half of the pupil of lens 80 and the pixel 83R is projected as 83R' on the right half of the pupil of lens 80, in the plan view. Although the single lens 80 is used herein, two left and right lenses may be used instead. In that case the pixels 83L, 83R are projected to the pupils of the respective lenses.

Figure 18:
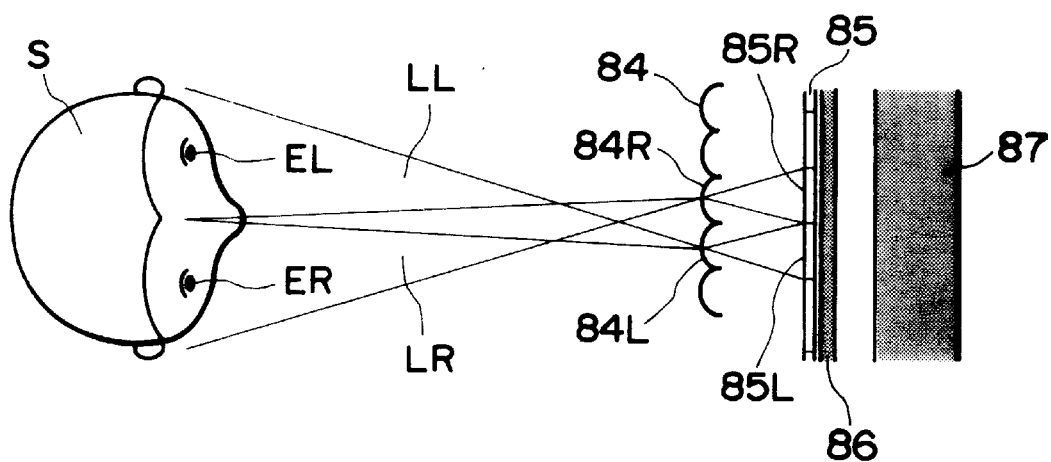
FIG. 18 is a plan view of observing means.

FIG. 18 is a plan view of observing means, in which cylindrical lens array 84, liquid-crystal image display member 85, diffuse plate 86, and back light source 87 are arranged in order in front of the observer S. The cylindrical lens array 84 has the almost same pitch as the pixels 85L, 85R of the image display member 85. For providing the cylindrical lens array 84 with the same prism action as the cylindrical lens array 82 of the photographing apparatus, the cylindrical lens array 84 is composed of pairs of cylindrical lens elements 84L and 84R with decentering in the direction to approach each other. The observer S is made conjugate with the image display member 85 in the plane view by the cylindrical lens elements 84L, 84R. With limitation to one observer S, the diffuse plate 86 does not have to be used.

When a stereoscopic image photographed by the photographing apparatus is observed through the observing means, the image is observed as magnified by the magnifying optical system in the case of the image photographed in the photographic film or the image is directly observed as displayed on the liquid-crystal monitor or the like with the cylindrical lens array in the case of the image picked up by the photographic medium 83. The object image picked up by the photographic medium 83 is once stored in a frame memory not illustrated and thereafter an inverted image is converted to an erect image to be displayed on the display member 85. The display member 85 is illuminated by the back light source 87 through the diffuse plate 86, and light outgoing from the display member element 85L is refracted by the cylindrical lens element 84L to become beam LL and reach the left eye EL of observer S. Similarly, light from the display member element 85R passes through the cylindrical lens element 84R to reach the right eye ER.

In this embodiment, since different portions on the object O correspond to the adjacent pixels 83L, 83R for the left and right eyes, there is no degradation of horizontal resolution due to the arrangement of stereoscopic vision. The left and right eyes EL, ER observe the object image consisting of vertical lines of mutually different portions and recognize the image position by the contours of the object image. The objects are perceived on the same plane if their contours are identical even though the lines of elements are different, the stereoscopic feeling can be made as long as there is a parallax between the contours of the left and right eye images.

As described above, when the stereoscopic photography stop is located near the pupil of the photographing optical system and the cylindrical lens array near the imaging plane of the photographing optical system, stereoscopic photography and monocular photography can be achieved by the simple structure.

When the cylindrical lens array or slit array of the pixel pitch, and the photographic, photosensitive medium are placed near the imaging plane of the imaging optical system, stereoscopic photography can be achieved by the photographing means of the simple structure, so that the apparatus can be made compact.

When the beams of the opposite phases are projected onto the left and right eyes of observer and the stereoscopic image is displayed by the cylindrical lens array, an appropriate position of a face can readily be determined upon observation.

When the stereoscopic image to be projected to the left and right eyes is displayed on the stereoscopic image display member composed of the alternate vertical stripe patterns of the pixel pitch and the stereoscopic image is projected to the screen having the cylindrical lens array of the pixel pitch, the stereoscopic image composed of the alternate vertical lines of the pixel pitch of the left and right eye images can be displayed as magnified for easier observation.

When the stereoscopic image to be projected to the left and right eyes is projected through the cylindrical lens array disposed near the stereoscopic image display member onto the screen having the field lens action for projecting the pupil of optical system to the observer, the apparatus can magnify and display the stereoscopic image to be observed readily.

When the images of the object viewed in two directions from left and right are focused at the pixel pitch with the generating lines extending vertically on the cylindrical lens array by the single photographing member, the photographing apparatus of the simple structure can be realized.

What is claimed is:

1. An eye imaging apparatus comprising:

illuminating means for illuminating an eye to be examined;

imaging optics for imaging the eye;

a camera for imaging the eye by way of the imaging optics;

optical means for laterally splitting the image of the eye provided in an optical path of said imaging optics leading to said camera, said optical means being arranged to be removable from the optical path.

2. An apparatus according to claim 1, wherein said optical means comprises a cylindrical lens array.

3. An apparatus according to claim 1, wherein said camera comprises a television camera.

4. A stereoscopic imaging apparatus comprising:

a collimating objective being common for stereoscopic optical paths;

optics for changing magnification, provided in each of the stereoscopic optical paths behind said collimating objective;

focusing optics being common for the stereoscopic optical paths for focusing collimated light from said optics;

a camera for imaging objects by way of the focusing optics; and optical means for laterally splitting the image of the objects to be imaged in said camera.

5. An apparatus according to claim 4, wherein said optical means comprises a cylindrical lens array.

6. An apparatus according to claim 4, wherein said camera comprises a television camera.

7. An eye imaging apparatus comprising:

illuminating means for illuminating an eye to be examined;

imaging optics for imaging the eye;

a camera for imaging the eye by way of the imaging optics;

a removable stereoscope stop placed in an optical path of said imaging optics leading to said camera, said stereoscope stop comprising a left stop and a right stop, and arranged so as to be removable; and a removable cylindrical lens array provided in the optical path of the imaging optics leading to said camera, said cylindrical lens array arranged to be removable from the optical path.

* * * * *

UNITED STATES PATENT AND TRADEMARK OFFICE
CERTIFICATE OF CORRECTION

PATENT NO. : 5,995,759
DATED : November 30, 1999
INVENTOR(S) : Yoshimi Kohayakawa Page 1 of 1

It is certified that error appears in the above-identified patent and that said Letters Patent is hereby corrected as shown below:

Title page,
Item [57] Abstract,
Line 1, "imagining" should read -- imaging --.

Column 5,
Line 12, "reversed:" should read -- reversed, --.

Column 8,
Line 27, "the almost" should read -- almost the --.

Column 10,
Line 2, "optics;" should read -- optics; and --.

Signed and Sealed this

Second Day of October, 2001

Attest:

NICHOLAS P. GODICI
Attesting Officer    Acting Director of the United States Patent and Trademark Office